United States Patent [19]

Buchecker et al.

[11] Patent Number: 5,360,577
[45] Date of Patent: Nov. 1, 1994

[54] OXAXOLINE DERIVATIVES

[75] Inventors: Richard Buchecker, Zurich; Stephen Kelly, Möhlin, both of Switzerland

[73] Assignee: Hoffmann-La Roche Inc., Nutley, N.J.

[21] Appl. No.: 946,987

[22] Filed: Sep. 17, 1992

[30] Foreign Application Priority Data

Sep. 26, 1991 [CH] Switzerland .......... 2862/91
Oct. 7, 1991 [CH] Switzerland .......... 2951/91
Apr. 7, 1992 [CH] Switzerland .......... 1128/92

[51] Int. Cl.$^5$ .......... C09K 19/34; C09K 19/30; C09K 19/20; C07D 26/10
[52] U.S. Cl. .......... 252/299.61; 252/299.62; 252/299.63; 252/299.66; 252/299.67; 548/237
[58] Field of Search .......... 252/299.01, 299.61, 252/299.62, 299.63, 299.66, 299.67; 548/237

[56] References Cited

U.S. PATENT DOCUMENTS 4,264,148  4/1981  Göbl-Wunsch et al. .......... 359/101
5,159,084  10/1992  Shoshi .......... 548/237

FOREIGN PATENT DOCUMENTS 3744024  12/1987  Germany .
3904797   2/1989  Germany .
4-29982   1/1992  Japan .

OTHER PUBLICATIONS

"Synthesis of Optically Active Bis(2-oxazolines): Crystal Structure of 1,2-Bis-(2-oxazolinyl)benzene.ZnCl$_2$Complex", Bolm et al.
Chem. Ber. 124, 1173–1180 (May 1991).
Derwent Abstract E13 L03 U11 V07 (1987) for DE-3744024.
Derwent Abstract E15 L03 U11 V07 (E14) (1989) for JP-027517.
Derwent Abstract E19 L03 (1989) for JP-023693.
Derwent Abstract AB9 E14 L03 (E13 E24) (1989) for DE-904797.
Derwent Abstract E13 L03 (E16) (1987) for JP-242077.
Derwent Abstract A32 E13 F01 (A23) (1986) for JP-017325.

Primary Examiner—Shean Wu
Attorney, Agent, or Firm—George M. Gould; William H. Epstein; Dennis P. Tramaloni

[57] ABSTRACT

Optically active compounds of the general formula

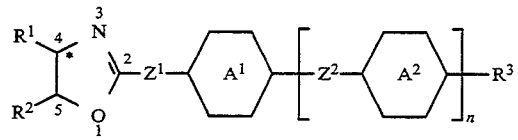

wherein n stands for the number 0 or 1; R$^3$ denotes a group R$^4$ or a group of the general formula

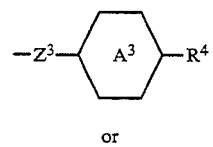

or

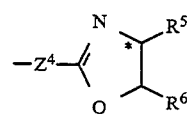

A$^1$, A$^2$ and A$^3$ each independently represent 1,4-phenylene, which is unsubstituted or mono- or multiply-substituted with halogen, cyano and/or methyl and in which, where it is unsubstituted, 1 or 2 CH groups is/are optionally replaced by nitrogen, trans-1,4-cyclohexylene, trans-1,3-dioxane-2,5-diyl, bycyclo[2.2.-2]octane-1,4-diyl, naphthalene-2,6-diyl, tetralin-2,6-diyl or trans-decalin-2,6-diyl; Z$^1$ and Z$^4$ each independently signify a single covalent bond or —CH$_2$CH$_2$—; Z$^2$ and Z$^3$ each independently denote a single covalent bond, —CH$_2$CH$_2$—, —COO—, —OOC—, —CH$_2$O—, —OCH$_2$—, —C≡C—, —(CH$_2$)$_4$—, —(CH$_2$)$_3$O—, —O(CH$_2$)$_3$— or the trans form of —CH=CH—CH$_2$CH$_2$—, —CH$_2$CH$_2$—CH=CH—, —CH=CH—CH$_2$O— or —OCH$_2$—CH=CH—; R$^1$ and R$^5$ each inde- (Abstract continued on next page.)

pendently signify alkyl with 1 to 12 carbon atoms, alkoxymethyl with 2 to 12 carbon atoms, p-alkoxyphenyl or p-alkoxybenzyl; $R^2$ and $R^6$ each independently signify hydrogen, alkyl with 1 to 12 carbon atoms or phenyl; $R^4$ denotes hydrogen, halogen, cyano, trifluoromethyl, trifluoromethoxy or alkyl or alkenyl with 1 to 12 and, respectively, 2 to 12 carbon atoms, which are unsubstituted or mono- or multiply-substituted with halogen, cyano and/or methyl and in which one methylene group or two non-adjacent methylene groups can be replaced by —O—, —COO— and/or —OOC—; and the oxazoline ring in formula I is present in optically active form, liquid crystalline mixtures which contain such dopants and their use for optical and electro-optical purposes.

5 Claims, No Drawings

OXAXOLINE DERIVATIVES

FIELD OF THE INVENTION

The invention is concerned with optically active dopants for liquid crystals and with liquid crystalline mixtures which contain such dopants and their use for optical and electro-optical purposes.

BACKGROUND OF THE INVENTION

Liquid crystal materials for electro-optical indicaters frequently contain one or more optically active additives for the induction of a chiral structure. For example, a nematic liquid crystal doped with an optically active additive is preferably used in indicators having a twisted nematic structure, e.g. to avoid a reversal of the direction of twisting (reverse twist) in TN cells (twisted-nematic) or in order to produce a sufficient twisting in cells having a highly twisted nematic structure such as STN cells (super twisted-nematic), SBE cells (super birefringence effect) or OMI cells (optical mode interference). Further, cholesteric liquid crystals for phase-change cells can preferably consist of a nematic basic material and one or more optically active dopants and ferroelectric liquid crystals for indicators based on chiral tilted smectic phases can preferably consist of a material having a tilted smectic phase and one or more optically active dopants.

The electro-optical characteristics of liquid crystal indicators are temperature-dependent, which is especially troublesome in the case of multiplex operation. It is, however, known that this temperature dependence can be compensated for at least partially by the addition of chiral dopants, which induce a pitch which decreases with increasing temperature. Such an inverse temperature dependence has hitherto been found only for a few compounds. It can, however, also be achieved by the use of at least two chiral dopants, which have a different relative temperature dependence and which induce a different twisting direction (U.S. Pat. No. 4,264,148). Of course, this requires for the most part a relatively high amount of chiral dopants.

Cholesteric liquid crystals reflect light in a wavelength range for which the wavelength is approximately equal to the helical pitch. The spectral width of this reflected light can be varied by a suitable choice of the liquid crystal. The reflected light is completely circularly polarized. The direction of rotation of the reflected light depends on the direction of rotation of the cholesteric helical structure. The light circularly polarized in the opposite direction is transmitted unimpaired. These properties can be utilized for the production of optical filters, polarizers, analyzers etc. Further, cholesteric liquid crystals have also variously been used for thermochromic applications and in cosmetic preparations.

Cholesteric liquid crystals for the above applications can preferably consist of a nematic or cholesteric basic material and one or more chiral dopants, which permits a simple adjustment of the desired helical pitch.

In order to produce cholesteric mixtures having a pitch in the range of the wavelength of visible light, the chiral dopants should have a twisting capacity which is as high as possible and should have a good solubility in usual liquid crystal materials. Furthermore, the chiral dopants should have an adequate stability, should have a good compatibility with the mesophase type of the liquid crystal material and should not restrict the mesophase range too severely. Such properties would also be desirable for chiral dopants for the production of the twisted nematic structures referred to earlier, since their amount can be held low in order that the properties of the liquid crystal material are influenced only immaterially.

SUMMARY OF THE INVENTION

The invention is directed to optically active compounds of the formula

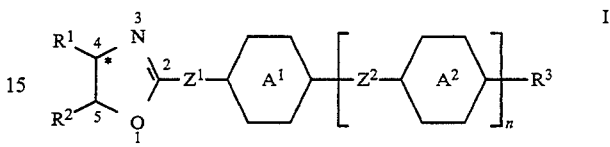

wherein n stands for the number 0 or 1; $R^3$ denotes a group $R^4$ or a group of the formula

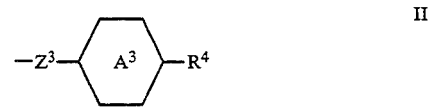

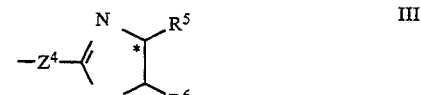

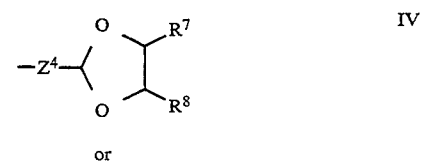

or

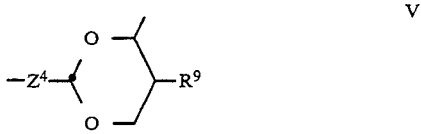

wherein $A^1$, $A^2$ and $A3$ each independently represent 1,4-phenylene, which is unsubstituted or mono- or multiply-substituted with halogen, cyano and/or methyl, and where the 1,4-phenylene is unsubstituted, 1 or 2 CH groups can be optionally replaced by nitrogen; trans-1,4-cyclohexylene; trans-1,3-dioxane-2,5-diyl; bycyclo[2.2.2]octane-1,4-diyl; naphthalene-2,6-diyl; tetralin-2,6-diyl or trans-decalin-2,6-diyl; $Z^1$ and $Z^4$ each independently are a single covalent bond or —CH$_2$CH$_2$—; $Z^2$ and $Z^3$ each independently denote a single covalent bond, —CH$_2$CH$_2$—, —COO—, —OOC—, —CH$_2$O—, —OCH$_2$—, —C≡C—, —(CH$_2$)$_4$—, —(CH$_2$)$_3$O—, —O(CH$_2$)$_3$— or the trans form of —CH═CH—CH$_2$CH$_2$—, —CH$_2$CH$_2$—CH═CH—, —CH═CH—CH$_2$O— or —OCH$_2$—CH═CH—; $R^1$ and $R^5$ each independently are alkyl with 1 to 12 carbon atoms, alkoxymethyl with 2 to 12 carbon atoms, p-alkoxyphenyl or p-alkoxybenzyl; $R^2$ and $R^6$ each independently is hydrogen, alkyl with 1 to 12 carbon atoms or phenyl; $R^7$ and $R^8$ each independently is hydrogen, alkyl with 1 to 12 carbon atoms, phenyl or alkoxycarbonyl with 2 to 12 carbon atoms, with the proviso that $R^7$ and $R^8$ do not simultaneously represent hydrogen; $R^9$ is alkyl with 1 to 9 carbon atoms or alkenyl with 2 to 9 carbon atoms, which alkyl or alkenyl are unsubstituted or mono- or multiply-substituted with fluorine and in which one —CH$_2$— group can be replaced by —O—; R$^4$ denotes hydrogen, halogen, cyano, trifluoromethyl, trifluoromethoxy or alkyl with 1 to 12 carbon atoms or alkenyl with 2 to 12 carbon atoms, which alkyl or alkenyl are unsubstituted or mono- or multiply-substituted with halogen, cyano and/or methyl and in which one methylene group or two non-adjacent methylene groups can be replaced by —O—, —COO— and/or —OOC—; and the oxazoline ring in formula I is present in optically active form.

DETAILED DESCRIPTION OF THE INVENTION

The invention relates to optically active compounds of the formula

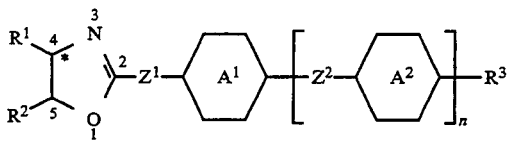

I wherein n stands for the number 0 or 1; R$^3$ denotes a group R$^4$ or a group of the formula

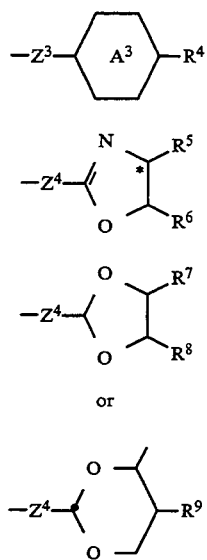

II

III

IV or

V wherein A$^1$, A$^2$ and A$^3$ each independently represent 1,4-phenylene, which is unsubstituted or mono- or multiply-substituted with halogen, cyano and/or methyl, and where the 1,4-phenylene is unsubstituted, 1 or 2 CH groups can be optionally replaced by nitrogen; trans-1,4-cyclohexylene; trans-1,3-dioxane-2,5-diyl; bycyclo[2.2.2]octane-1,4-diyl; naphthalene-2,6-diyl; tetralin-2,6-diyl or trans-decalin-2,6-diyl; Z$^1$ and Z$^4$ each independently are a single covalent bond or —CH$_2$CH$_2$—; Z$^2$ and Z$^3$ each independently denote a single covalent bond, —CH$_2$CH$_2$—, —COO—, —OOC—, —CH$_2$O—, —OCH$_2$—, —C≡C—, —(CH$_2$)$_4$—, —(CH$_2$)$_3$O—, —O(CH$_2$)$_3$— or the trans form of —CH=CH—CH$_2$CH$_2$—, —CH$_2$CH$_2$—CH=CH—, —CH=CH—CH$_2$O— or —OCH$_2$—CH=CH—; R$^1$ and R$^5$ each independently are alkyl with 1 to 12 carbon atoms, alkoxymethyl with 2 to 12 carbon atoms, p-alkoxyphenyl or p-alkoxybenzyl; R$^2$ and R$^6$ each independently is hydrogen, alkyl with 1 to 12 carbon atoms or phenyl; R$^7$ and R$^8$ each independently is hydrogen, alkyl with 1 to 12 carbon atoms, phenyl or alkoxycarbonyl with 2 to 12 carbon atoms, with the proviso that R$^7$ and R$^8$ do not simultaneously represent hydrogen; R$^9$ is alkyl with 1 to 9 carbon atoms or alkenyl with 2 to 9 carbon atoms respectively, which alkyl or alkenyl are unsubstituted or mono- or multiply-substituted with fluorine and in which one —CH$_2$— group can be replaced by —O—; R$^4$ denotes hydrogen, halogen, cyano, trifluoromethyl, trifluoromethoxy or alkyl with 1 to 12 carbon atoms or alkenyl with 2 to 12 carbon atoms respectively, which alkyl or alkenyl are unsubstituted or mono- or multiply-substituted with halogen, cyano and/or methyl and in which one methylene group or two non-adjacent methylene groups can be replaced by —O—, —COO— and/or —OOC—; and the oxazoline ring in formula I is present in optically active form.

The compounds of formula I have very good solubility in usual liquid crystal materials and permit very high twisting of the liquid crystal structure. In contrast to known materials having high twisting capacities, the clearing points of liquid crystals with the addition of compounds of formula I are as a rule not lowered or are lowered only immaterially. Many of the compounds in accordance with the invention themselves even have liquid crystalline properties. The compounds of formula I can be produced readily, have a relatively low viscosity and are sufficiently stable to electric and magnetic fields. They therefore fulfil in an optimum manner the requirements referred to above.

The properties of the compounds of formula I can be varied in a wide range depending on the number and significance of the rings and of the substituents. For example, aromatic rings lead to high values of the optical anisotropy and saturated rings lead to low values of the optical anisotropy. A clearing point increase can be achieved, for example, by the introduction of an additional ring. Accordingly, compounds of formula I in which n signifies the number 1 and/or R$^3$ signifies a group of formula II often have liquid crystalline properties themselves. Polar end groups such as cyano, halogen, trifluoromethyl or trifluoromethoxy and rings such as pyrimidine-2,5-diyl or trans-1,3-dioxane-2,5-diyl increase the dielectric anisotropy; rings such as pyridazine-3,6-diyl or 2,3-dicyano-1,4-phenylene reduce the dielectric anisotropy. Lateral halogen or cyano substitutents contribute to the dielectric constant not only parallel to, but also perpendicular to the longitudinal axis of the molecule, which, depending on the substitution pattern, can be utilized to increase or reduce the dielectric anisotropy. Further, a possible tendency to form highly ordered smectic phases can often largely be suppressed and the solubility can also often be improved by lateral substituents on one or more rings. Furthermore, the elastic properties, the threshold potentials, the response times, the mesophases etc. can be modified further by a C═C double bond in the side-chain.

The compounds in accordance with the invention therefore also permit, in addition to the induction of high twisting, the ability to optimize liquid crystalline and electro-optical properties in a wide range according to application and desired properties.

As used herein, the term "halogen" denotes fluorine, chlorine, bromine or iodine. Preferred are fluorine or chlorine.

What is meant by the term "1,4-phenylene, which is unsubstituted or mono- or multiply-substituted with halogen, cyano and/or methyl and when the 1,4-phenylene is unsubstituted, 1 or 2 CH groups is/are optionally replaced by nitrogen" are groups such as 1,4-phenylene, 2-fluoro-1,4-phenylene, 2,3-difluoro-1,4-phenylene, 2-chloro-1,4-phenylene, 2-bromo-1,4-phenylene, 2-cyano-1,4-phenylene, 2,3-dicyano-1,4-phenylene, 2-methyl-1,4-phenylene, pyridine-2,5-diyl, pyrazine-2,5-diyl, pyrimidine-2,5-diyl, pyridazine-3,6-diyl, and the like. 1,4-Phenylene, 2-fluoro-1,4-phenylene, 2,3-difluoro-1,4-phenylene, pyridine-2,5-diyl, pyrazine-2,5-diyl and pyrimidine-2,5-diyl are preferred groups.

The term "tetralin-2,6-diyl" denotes 1,2,3,4-tetrahydronaphthalene-2,6-diyl. The term "trans-decalin-2,6-diyl" embraces 2,6-disubstituted groups derived from trans-decahydronaphthalene, especially (4a$\alpha$H,7a$\beta$H)-decahydronaphthalene-2$\alpha$,6$\beta$-diyl.

The term "alkyl" embraces straight-chain and branched, optionally chiral groups, with 1–12 carbon atoms such as methyl, ethyl, propyl, isopropyl, butyl, isobutyl, tert.butyl, 2-butyl (same as methylpropyl), 2-methylbutyl, pentyl, hexyl, heptyl, octyl, 2-octyl (same as 1-methylheptyl), nonyl, decyl, undecyl, dodecyl and the like. Alkyl residues with 1 to 7 carbon atoms, especially alkyl residues with 1 to 5 carbon atoms such as, for example, methyl, isopropyl and tert-.butyl, are preferred.

The term "alkoxymethyl" embraces straight-chain and branched, optionally chiral groups with 2 to 12, preferably 2 to 7, carbon atoms such as, for example, methoxymethyl, ethoxymethyl, propyloxymethyl, butyloxymethyl, isopropyloxymethyl, tert.-butyloxymethyl and the like; those residues with 2 to 5 carbon atoms are especially preferred.

The term "alkoxycarbonyl" embraces straight-chain and branched, optionally chiral groups with 2–12 carbon atoms such as methoxycarbonyl, ethoxycarbonyl, propyloxycarbonyl, isopropyloxycarbonyl, butyloxycarbonyl, isobutyloxycarbonyl, (2-butyl)oxycarbonyl, (2-methylbutyl)oxycarbonyl, pentyloxycarbonyl, hexyloxycarbonyl and the like. Groups with 2 to 7 carbon atoms are preferred.

In the terms "p-alkoxyphenyl" and "p-alkoxybenzyl", alkoxy signifies a straight-chain or a branched, optionally chiral, residue with 1 to 7 carbon atoms. Examples of preferred p-alkoxyphenyl- and p-alkoxybenzyl-groups are 4-methoxyphenyl, 4-ethoxyphenyl, 4-propyloxyphenyl, 4-butyloxyphenyl, 4-pentyloxyphenyl, 4-hexyloxyphenyl, 4-heptyloxyphenyl, 4-methoxybenzyl, 4-ethoxybenzyl, 4-propyloxybenzyl, 4-butyloxybenzyl, 4-pentyloxybenzyl, 4-hexyloxybenzyl, 4-heptyloxybenzyl and the like.

As used herein the term "alkyl with 1 to 9 carbon atoms or alkenyl with 2 to 9 carbon atoms respectively, which is unsubstituted or mono- or multiply-substituted with fluorine and in which one —$CH_2$— group can be replaced by —O—", signifies straight-chain and branched (optionally chiral) residues with 1 to 9 and, respectively, 2 to 9 carbon atoms such as alkyl, 3E-alkenyl, 4-alkenyl, alkenyl having a terminal double bond, alkoxy, 2E-alkenyloxy, 3-alkenyloxy, alkenyloxy having a terminal double bond, alkoxyalkyl, alkenyloxyalkyl, alkoxyalkenyl, fluoroalkyl and the like. Residues with 1 to 7 carbon atoms and, respectively, 2 to 7 carbon atoms are preferred. Methyl, ethyl, propyl, butyl, pentyl, hexyl, heptyl, 1-methylpropyl, 2-methylbutyl, 3-methylpentyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, methoxy, ethoxy, propyloxy, butyloxy, pentyloxy, hexyloxy, heptyloxy, 1-methylpropyloxy, 2-methylbutyloxy, 3-methylpentyloxy, allyloxy, 2E-butenyloxy, 2E-pentenyloxy, 2E-hexenyloxy, 2E-heptenyloxy, 3butenyloxy, 3Z-pentenyloxy, 3Z-hexenyloxy, 3Z-heptenyloxy, 4-pentenyloxy, 5-hexenyloxy, 6-heptenyloxy, methoxymethyl, ethoxymethyl, propyloxymethyl, allyloxymethyl, 2-fluoroethyl, 3-fluoropropyl, 4-fluorobutyl, 5-fluoropentyl, 6-fluorohexyl, 1-fluoropropyl, 1-fluoropentyl, 2fluoropropyloxy, 2-fluoro-butyloxy, 2-fluoropentyloxy, 2-fluorohexyloxy, 2-fluorobutyloxy and the like are examples of preferred residues. It is especially preferred that the aforementioned residues have 1 to 5 carbon atoms and, respectively, 2 to 5 carbon atoms.

The term "alkyl or alkenyl, which alkyl or alkenyl is unsubstituted or mono- or multiply-substituted with halogen, cyano and/or methyl and in which one methylene group or two non-adjacent methylene groups can be replaced by —O—, —COO— and/or —OOC—" embraces straight-chain and branched (optionally chiral) alkyl residues with 1 to 12 carbon atoms and, alkenyl residues with 2 to 12 carbon atoms such as alkyl, 1E-alkenyl, 3E-alkenyl, 4-alkenyl, alkenyl having a terminal double bond, alkoxy, 2E-alkenyloxy, 3-alkenyloxy, alkenyloxy having a terminal double bond, alkoxyalkyl, alkenyloxyalkyl, alkoxycarbonyl, alkoxycarbonylalkoxy (e.g. (1-alkoxycarbonyl)-1-ethoxy), alkoxycarbonylalkoxycarbonyl (e.g. (1-alkoxycarbonyl)-1-ethoxy-carbonyl), alkanoyloxy, 1-haloalkyl, 2-haloalkyl, 2-haloalkoxy, 2-haloalkoxycarbonyl, 1-cyanoalkyl, 2-cyanoalkyl, 2cyanoalkoxy, 2-cyanoalkoxycarbonyl, 1-methylalkyl, 2-methylalkyl, 1-methylalkoxy, 2-methylalkoxy, 2-methylalkoxycarbonyl and the like. Methyl, ethyl, propyl, butyl, pentyl, hexyl, heptyl, octyl, nonyl, decyl, undecyl, dodecyl, 1-methylpropyl, 1-methylheptyl, 2-methylbutyl, 3-methylpentyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, 1-methylpropyloxy, 1-methylheptyloxy, 2-methylbutyloxy, 3-methylpentyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, allyloxymethyl, methoxycarbonyl, ethoxycarbonyl, propyloxycarbonyl, 1-methylpropyloxycarbonyl, 1-(methoxycarbonyl)ethoxy, 1-(ethoxycarbonyl)ethoxy, 1-(methoxycarbonyl)ethoxycarbonyl, 1-(ethoxy-carbonyl)ethoxy-carbonyl, 1-(isopropyloxycarbonyl)ethoxycarbonyl, 1-(butyloxycarbonyl)ethoxycarbonyl, acetoxy, propionyloxy, butyryloxy, 1-fluoropropyl, 1-fluoropentyl, 1-chloropropyl, 2-fluoropropyl, 2-fluoropentyl, 2-chloropropyl, 2-fluoropropyloxy, 2-fluorobutyloxy, 2-fluoropentyloxy, 2fluorohexyloxy, 2-chloropropyloxy, 2-fluorobutyloxy, 2-fluoropropyloxycarbonyl, 2- fluorobutyloxycarbonyl, 2-fluoropentyloxycarbonyl, 2-fluoro-3methylbutyloxycarbonyl, 2-fluoro-4-methyl-pentyloxycarbonyl, 2-chloropropyloxycarbonyl, 1-cyanopropyl, 1-cyanopentyl, 2-cyanopropyl, 2-cyanopentyl, 2-cyanopropyloxy, 2-cyanobutyloxy, 2-cyanopentyloxy, 2-cyanohexyloxy, 2-cyanopropyloxycarbonyl, 2-cyanobutyloxycarbonyl, 2-cyano-3methylbutyloxycarbonyl, 2-cyano-4-methylpentyloxycarbonyl and the like are examples of preferred residues. Preferably, the aforementioned alkyl residues have 1 to 12 carbon atoms and, the alkenyl residues have 2 to 12 carbon atoms. Alkyl residues of $R^4$ with 1 to 7 carbon atoms and, alkenyl residues of 2 to 7 carbon atoms are especially preferred.

Formula I embraces optically active compounds of the following formulas

I-1

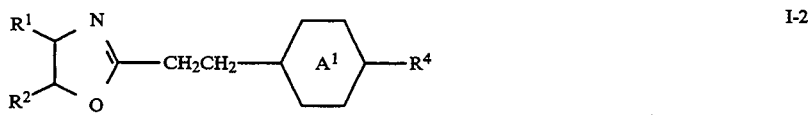

I-2

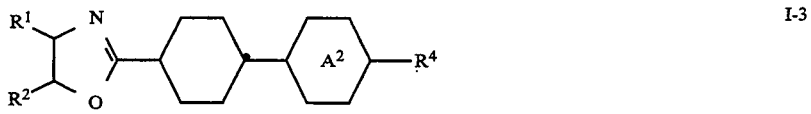

I-3

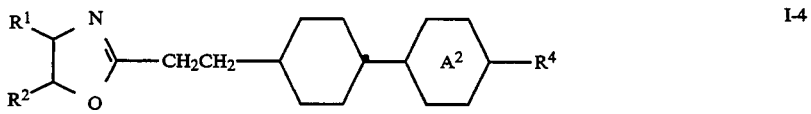

I-4

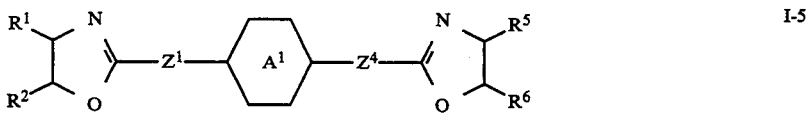

I-5

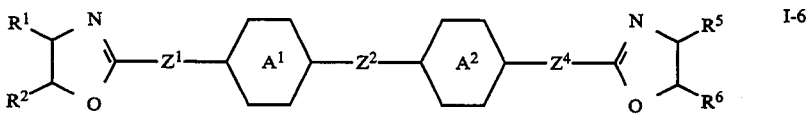

I-6

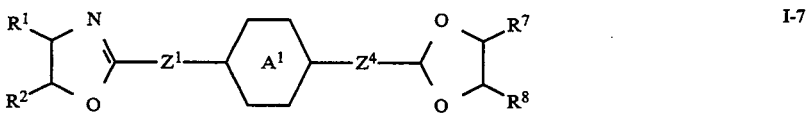

I-7

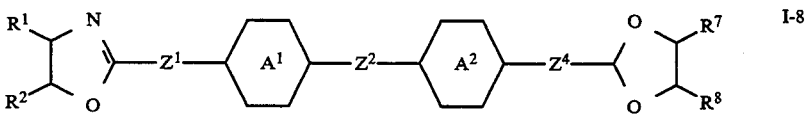

I-8

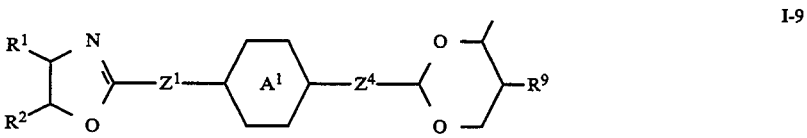

I-9

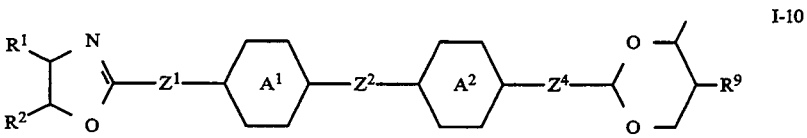

I-10 wherein $R^1$, $R^2$, $R^4$, $R^5$, $R^6$, $R^7$, $R^8$, $R^9$, $A^1$, $A^2$, $Z^1$, $Z^2$ and $Z^4$ have the above definitions.

The compounds of formula I have at least one optically active oxazoline ring. The oxazoline ring in formula I has a chiral carbon atom in position 4 and, where $R^2$ is different from hydrogen, a further chiral carbon atom in position 5. It will be evident to a person skilled in the art that in order to achieve optical activity the carbon atom in position 4 of the oxazoline ring must be present completely or predominantly in the R- or S-form and, where $R^1$ and $R^2$ are identical, the carbon atom in position 5 of the oxazoline ring should have completely or predominantly the same configuration as the carbon atom in position 4 or basically can also have a R/S ratio of 50:50. In order to achieve a twisting capacity which is as high as possible, the carbon atom in position 4 of the oxazoline ring should preferably be present in the R- or S-configuration in the optically purest form possible and, where $R^2$ is different from hydrogen, the carbon atom in position 5 of the oxazoline ring should preferably be present in either configuration and in the optically purest form as possible, which increases the twisting capacity. Preferred optical isomers having a high twisting capacity are the (4R)-isomers and the (4S)-isomers of the compounds of formula I in which $R^2$ signifies hydrogen and the (4R,5R)-isomers and the (4S,5S)-isomers of the compounds of formula I in which $R^2$ signifies alkyl or phenyl.

Especially preferred are those compounds of formula I and, respectively, I-1 to I-10 in which $A^1$, $A^2$ and $A^3$ each independently represent 1,4-phenylene, which is unsubstituted or mono- or multiply-substituted with halogen, cyano and/or methyl (especially 1,4-phenylene, 2-fluoro-1,4-phenylene or 2,3-difluoro-1,4-phenylene), or trans-1,4-cyclohexylene. Alternatively, one of groups $A^1$, $A^2$ and $A^3$ also represents pyrimidine-2,5-diyl or pyridine-2,5-diyl and, further, one of the optionally present groups $Z^2$ and $Z^3$ denotes a single covalent bond, —CH$_2$CH$_2$—, —COO— or —OOC— (especially a single covalent bond) and, where present, the other of groups $Z^2$ and $Z^3$ denotes a single covalent bond. These compounds are very stable and as a rule are especially readily synthesized from known liquid crystal intermediates.

The twisting capacity of the compounds in accordance with the invention is determined mainly by the optically active oxazoline residue; it will thus be evident that the preferred rings and bridging groups named just above have an influence on the liquid crystalline properties of the compounds only and thus can be replaced by other rings specified for $A^1$, $A^2$ and $A^3$ in formula I and bridging groups specified for $Z^2$ and $Z^4$ in formula I in order to achieve a similar effect and likewise good compatibility with usual liquid crystals.

$Z^1$ and $Z^2$ in formulae I and, respectively, I-1 to I-10 above can have the same significance or different significances. Preferably, $Z^1$ and/or $Z^2$ stands for a single covalent bond.

The optically active compounds of the following formulas are examples of especially preferred compounds of formula I

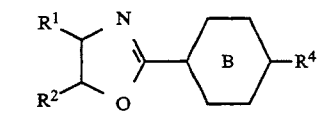
I-11

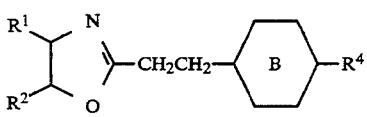
I-12

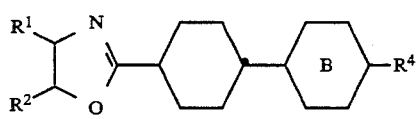
I-13

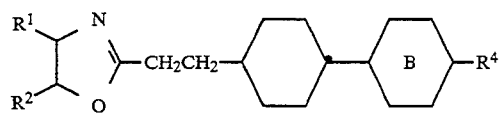
I-14

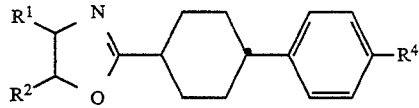
I-15

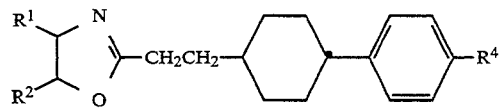
I-16

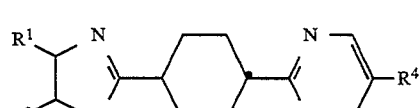
I-17

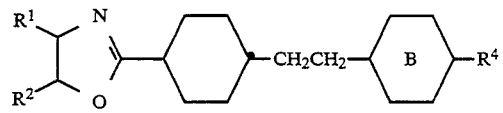
I-18

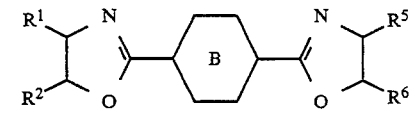
I-19

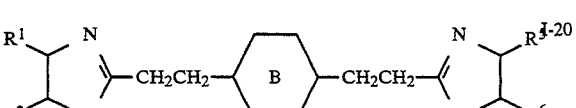
I-20

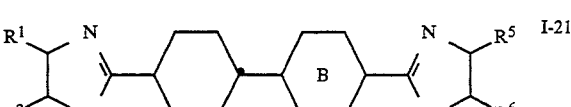
I-21 wherein $R^1$, $R^2$, $R^4$, $R^5$ and $R^6$ have the above significances and ring B represents 1,4-phenylene, which is unsubstituted or mono- or multiply-substituted with halogen (preferably 1,4-phenylene, 2-fluoro-1,4-phenylene or 2,3-difluoro-1,4-phenylene), or trans-1,4-cyclohexylene.

In formulas I, I-1 to I-4 and I-11 to I-19 above, $R^4$ preferably denotes halogen (especially fluorine or chlorine), cyano, trifluoromethyl, trifluoromethoxy, alkyl, alkenyl, alkoxy or alkenyloxy. However, if desired, in an alkyl residue $R^4$ one methylene group or two non-adjacent methylene groups can be replaced by —O—, —COO— and/or —OOC— and/or one methylene group can be replaced by —CHX— (wherein X signifies halogen, cyano or methyl). This possibility can be utilized e.g. to increase the twisting capacity by the introduction of chiral groups staring from simple, optically active compounds. Preferred examples of such groups are the residues derived from optically active lactic acid such as 1-(alkoxycarbonyl)ethoxy and 1-(alkoxycarbonyl)ethoxycarbonyl. $R^4$ in the above formula can therefore preferably also signify one of these residues.

$R^4$ stands for alkyl- and alkenyl-groups with 1 to 12 carbon atoms and, respectively 2 to 12 carbon atoms. Preferred residues $R^4$ are those with 1 to 7 carbon atoms and, respectively, 2 to 7 carbon atoms, especially those with 1 to 5 carbon atoms and, respectively, 2 to 5 carbon atoms.

The compounds of formula I can, also contain an end group of formula III, i.e. an additional oxazoline residue. This group can be optically inactive. However, there are preferred groups of formula III which are present in an optically active form, which increases the twisting capacity. Such compounds having an increased twisting capacity, which can also be produced especially readily, are those in which both oxazoline rings have the same configuration and the same substituents. Preferably, therefore, in formula III $R^5$ has the same significance and at the adjacent C atom the same configuration as $R^1$ and $R^6$ has the same significance and at the adjacent C atom the same configuration as $R^2$. This also accordingly applies to the two oxazoline residues in formulae I-5, I-6, I-19, I-20, I-21 and I-22.

Of the compounds of formula I in which $R^3$ signifies a group of formula IV or of formula V (i.e. I-7, I-8, I-9 and I-10) there are preferred those in which the dioxane ring (formula IV) and, respectively, the dioxane ring (formula V) is present in optically active form.

$R^7$ and $R^8$ have, when different from hydrogen and phenyl, 1 to 12 carbon atoms. In general, there are preferred residue $R^7$ and $R^8$ with 1 to 7 carbon atoms, but especially those with 1 to 5 carbon atoms.

The residue $R^9$ has 1 to 9 carbon atoms. Especially preferred residues of $R^9$ have 1 to 5 carbon atoms.

Preferred optical isomers are therefore the compounds having the relative configuration given in the following formula

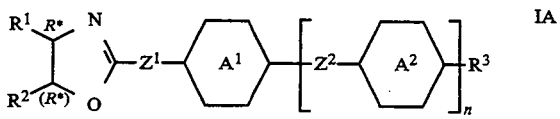  IA wherein $R^3$ denotes a group $R^4$ or a group of the formula

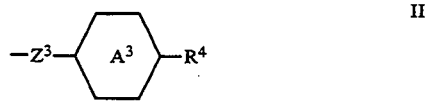  II

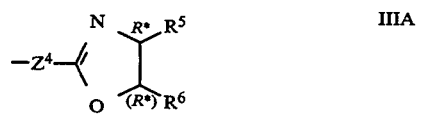  IIIA

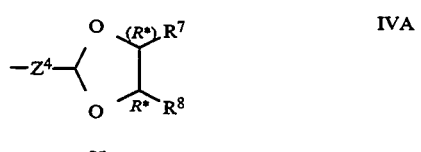  IVA or

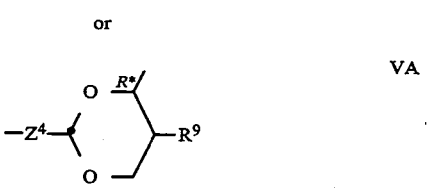  VA n, $A^1$, $A^2$, $A^3$, $Z^1$, $Z^2$, $Z^3$, $Z^4$, $R^1$, $R^2$ and $R^4$, $R^5$, $R^6$, $R^7$, $R^8$ and $R^9$ have the above significances; the chiral center (R*) is absent when $R^2$ signifies hydrogen and stands for R* when $R^2$ is different from hydrogen; and the asymmetric carbon atoms denoted by R* are all present in the R-configuration or are all present in the S-configuration.

Formula IA embraces the optical isomers indicated by R* as well as their optical antipodes (S-form) which have the same twisting capacity, but with opposite direction of twisting.

Preferred optically active compounds of formula IA are those in which $R^1$ and $R^2$ have different significances or preferably the same significance. Especially preferred are compounds wherein $R^1$ denotes $C_1$-$C_5$-alkyl, p-alkoxy-phenyl or p-alkoxybenzyl, especially isopropyl and tert.butyl. These compounds are readily accessible from the corresponding, optically active 2-amino-1-ethyl alcohols. Those compounds of formulae I-1 to I-21 in which $R^1$ denotes isopropyl or tert.butyl and $R^2$ denotes hydrogen are especially preferred with regard to their preparation.

In formula IA above and in the sub-groups of compounds of formula I referred to above as being preferred rings $A^1$, $A^2$, $A^3$, ring B, the bridging groups $Z^1$, $Z^2$, $Z^3$, $Z^4$ especially have the preferred significances given in connection with formulas I and I-1 to I-21.

The compounds in accordance with the invention can be readily produced in a manner known per se. They can be produced, for example, by reaching an acid chloride of the formula $Cl.OC-Z^1-A^1-(Z^2-A^2)_n-R^3$ with an optically active aminoalcohol of the formula $R^1-CH(NH_2)-CH(OH)-R^2$. The reaction of the acid chloride with the aminoalcohol can be effected in a manner known per se. Conveniently, the reaction is effected in an inert organic solvent (for example dichloromethane). Temperature and pressure are not critical, but the reaction is preferably carried out at 0° C. and atmospheric pressure. The formation of the oxazoline ring can be effected in a manner known per se. Conveniently, the reaction is effected in an inert solvent (for example dichloromethane) in the presence of thionyl chloride.

An optionally present second oxazoline ring (when $R^3$ signifies a group of formula III) can be formed in analogous manner, likewise from an acid chloride and aminoalcohol. If both aminoalcohols [$R^1-CH(NH_2)-CH(OH)-R^2$ and $R^5-CH(NH_2)-CH(OH)-R^6$] are identical, both oxazoline rings can, if desired, be formed in one step.

If the compound of formula I contains one or more ester groups in $Z^2$, $Z^3$ and/or $R^4$, then the esterification can preferably be effected after the oxazoline ring has been formed. If desired, ether groups and other functional groups can also be introduced after the oxazoline ring has been formed.

Such methods will basically be known to a person skilled in the art, e.g. from the production of liquid crystalline dioxanes. The aminoalcohols required as starting materials are known compounds or are analognes of known compounds. The acid chlorides required as starting materials are also known compounds or can be prepared according to methods known per se. Such compounds and methods are e.g. known from U.S. Pat. Nos. 4,676,604, 4,621,901 and EP-A-0168683.

The invention is also concerned with liquid crystalline mixtures containing a liquid crystalline carrier material and one or more optically active compounds of formula I. Suitable carrier materials are all liquid crystal materials which have a twistable liquid crystal phase with an adequate mesophase range. The compounds of formula I are especially suitable as chiral dopants for nematic or cholesteric carrier materials. The liquid crystalline carrier material can be a single compound or a mixture and preferably has a clearing point of at least about 60° C.

The content of chiral dopant of formula I is determined essentially by its twisting capacity and the desired pitch. The content of chiral dopant can therefore vary in a wide range according to application and can be, for example, about 0.1–30 wt. %. Depending on the type and thickness of cell, a pitch of about 3–40 mm is mainly required for indicators based on liquid crystal having a twisted nematic structure and therefore a correspondingly smaller content is sufficient. On the other hand, for applications which are based on the reflection of visible light by cholesteric layers, pitches of less than 2 mm, for example about 0.4–0.6 mm, are necessary and this requires a correspondingly higher content of chiral dopant.

Suitable liquid crystalline carrier materials are known in large numbers and are commercially available. As a rule, liquid crystalline mixtures containing two or more components are preferred carrier materials. Basically, however, a liquid crystalline compound can be used as the carrier material when it has a sufficiently broad mesophase.

Compounds of the following formulas are especially suitable as components for liquid crystalline carrier materials

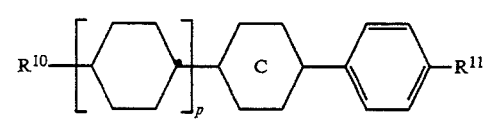 VI

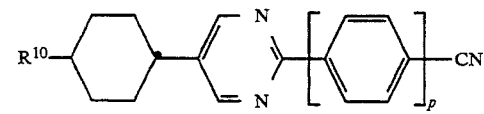 VII

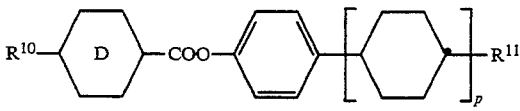 VIII

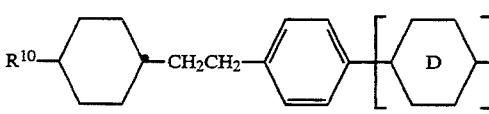 IX

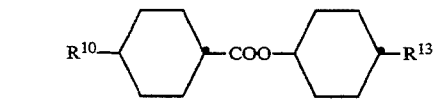 X

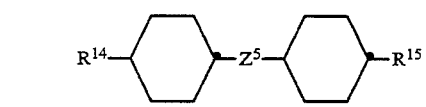 XI

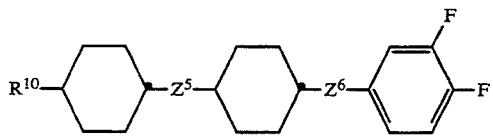 XII

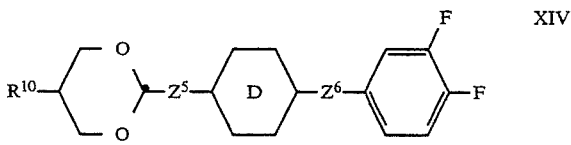 XIII

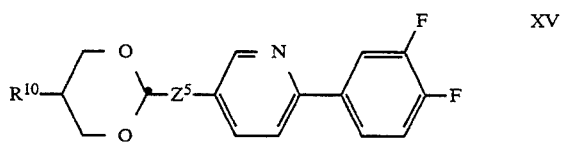 XIV

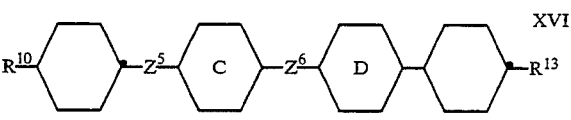 XV

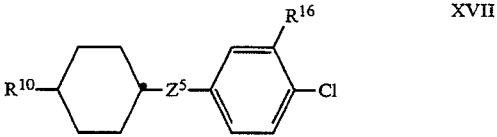 XVI

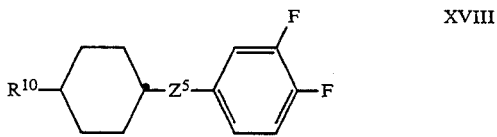 XVII

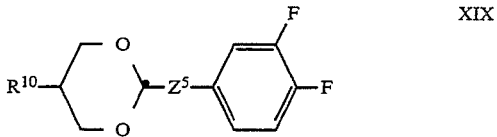 XVIII

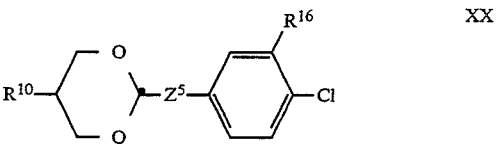 XIX

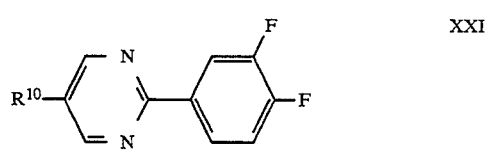 XX

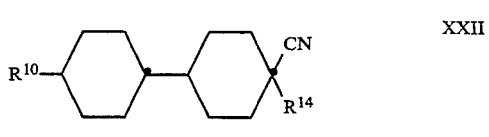 XXI

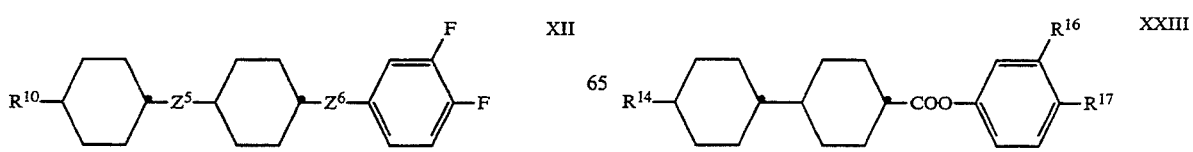 XXII

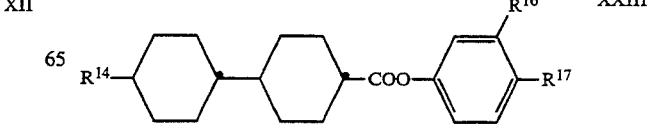 XXIII

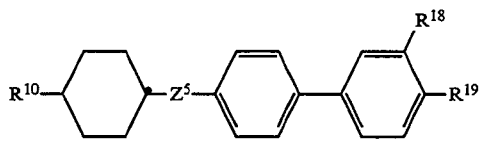

wherein $R^{10}$ and $R^{13}$ signify alkyl, alkoxyalkyl, 3E-alkenyl, 4-alkenyl or on saturated rings also 1E-alkenyl; p signifies 0 or 1; ring C denotes 1,4-phenylene, pyridine-2,5-diyl, pyrimidine-2,5-diyl, trans-1,4-cyclohexylene or trans-1,3-dioxane-2,5-diyl; $R^{11}$ represents cyano, isothiocyanato, fluorine, alkyl, 3E-alkenyl, 4-alkenyl, alkoxy, 2E-alkenyloxy, 3-alkenyloxy or 1-alkynyl; ring D signifies 1,4-phenylene or trans-1,4-cyclohexylene; $R^{12}$ denotes alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy; $R^{14}$ signifies alkyl, 1E-alkenyl, 3E-alkenyl or 4-alkenyl; $R^{15}$ represents cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl; $Z^5$ and $Z^6$ denote a single covalent bond or —$CH_2CH_2$—, whereby two aromatic rings are always linked by a single covalent bond; $R^{16}$ signifies hydrogen, fluorine or chlorine; $R^{17}$ represents cyano, fluorine or chlorine; $R^{18}$ denotes hydrogen or fluorine; $R^{19}$ represents fluorine or chlorine.

$R^{10}$, $R^{11}$, $R^{12}$, $R^{13}$, $R^{14}$ and $R^{15}$ each have a maximum of 12 carbon atoms, preferably a maximum of 7 carbon atoms. 1E-Alkenyl, 3E-alkenyl and 4Z-alkenyl are preferred alkenyl groups. 2E-Alkenyloxy and 3Z-alkenyloxy are preferred alkenyloxy groups.

The invention is illustrated in more detail by the following Examples.

In connection with liquid crystal phases and phase transitions, C signifies a crystalline phase, $S_B$ signifies a smectic B phase, N signifies a nematic phase, N* signifies a cholesteric phase and I signifies the isotropic phase. The helical pitch is denoted by p and the wavelength of the selectively reflected, circularly polarized light is denoted by $l_{max}$. Optical antipodes have in each case "mirror image properties", i.e. the same melting points etc, but lead to the opposite helical rotation and opposite circular polarization of the reflected light. Unless indicated otherwise, the Examples were carried out as written.

EXAMPLE 1

A suspension of 1.05 g of 4-(trans-4-heptylcyclohexyl)-N-[(S)-2-hydroxy-1-isopropylethyl)benzamide in 40 ml of acetenitrile was treated dropwise with 0.7 ml of thionyl chloride at 0° C. and while gassing with nitrogen. The reaction mixture was stirred at 0° C. overnight, poured into 100 ml of saturated potassium carbonate solution and then extracted three times with 50 ml of diethyl ether each time. The combined organic phases were washed twice with 50 ml of saturated sodium chloride solution each time, dried over magnesium sulphate, filtered and subsequently concentrated. Chromatography of the residue on silica gel with hexane/ethyl acetate (vol. 2:1) and recrystallization from acetone at −25° C. gave pure (S)-2-[4-(trans-4-heptylcyclohexyl)phenyl]-4-isopropyl-2-oxazoline with m.p. (C-I) 51° C. and cl.p. (S-I) 46° C.

The 4-(trans-4-heptylcyclohexyl)-N-[(S)-2-hydroxy-1-isopropylethyl)benzamide used as the starting material was prepared as follows:

2.1 g of 4-(trans-4-heptylcyclohexyl)benzoic acid were heated at 80° C. for 1 hour with 10 ml of thionyl chloride in toluene. The solution obtained was evaporated under reduced pressure, the residue was treated with 20 ml of absolute toluene and the solution was again evaporated under reduced pressure. The acid chloride obtained was taken up in 50 ml of dichloromethane and added dropwise to a solution of 1.45 g of S(+)-2-amino-3-methyl-1-butanol in 20 ml of dichloromethane at 0° C. and while gassing with nitrogen. The reaction mixture was stirred at room temperature overnight, then poured into 100 ml of potassium carbonate, stirred intensively for 5 minutes, then extracted three times with 50 ml of diethyl ether each time. The combined organic phases were washed twice with 100 ml of saturated sodium chloride solution each time, dried over magnesium sulphate, filtered and subsequently concentrated. This gave 1.05 g of 4-(trans-4-heptylcyclohexyl)-N-[(S)-2-hydroxy-1-isopropylethyl)benzamide.

The following compounds can be produced in an analogous manner:

(S)-2-[4-(trans-4-Propylcyclohexyl)phenyl]-4-isopropyl-2-oxaxoline;

(S)-2-[4-(trans-4-pentylcyclohexyl)phenyl]-4-isopropyl-2-oxaxoline;

(S)-2-[4-(trans-4-propylcyclohexyl)phenyl]-4-tert.butyl-2-oxaxoline;

(S)-2-[4-(trans-4-pentylcyclohexyl)phenyl]-4-tert.butyl-2-oxaxoline;

(S)-2-[4-(trans-4-heptylcyclohexyl)phenyl]-4-tert.butyl-2-oxaxoline;

(S)-2-[4-(trans-4-vinylcyclohexyl)phenyl]-4-isopropyl-2-oxaxoline;

(S)-2-[4-(trans-4-allylcyclohexyl)phenyl]-4-isopropyl-2-oxaxoline;

(S)-2-[4-(trans-4-(3-butenyl)cyclohexyl)phenyl]-4-isopropyl-2-oxaxoline;

(S)-2-[4-(trans-4-(1-pentenyl)cyclohexyl)phenyl]-4-isopropyl-2-oxaxoline;

(S)-2-[4-(trans-4-(3-pentenyl)cyclohexyl)phenyl]-4-isopropyl-2-oxaxoline;

(S)-2-[4-(trans-4-(4-pentenyl)cyclohexyl)phenyl]-4-isopropyl-2-oxaxoline;

(S)-2-[4-(5-pentyl-2-pyrimidinyl)phenyl]-4-isopropyl-2-oxazoline, m.p. 113° C.;

(S)-2-[4-(trans-4-propylcyclohexyl)-4'-biphenyl]-4-isopropyl-2-oxaxoline;

(S)-2-[4-(trans-4-pentylcyclohexyl)-4'-biphenyl]-4-isopropyl-2-oxaxoline, m.p. C-$S_B$ 132° C., $S_B$-$S_A$ 175° C., cl.p. ($S_A$-I) 210° C.;

(S)-2-[4-(trans-4-heptylcyclohexyl)-4'-biphenyl]-4-isopropyl-2-oxaxoline;

(S)-2-[4-(trans-4-propylcyclohexyl)-4'-biphenyl]-4-tert.butyl-2-oxaxoline;

(S)-2-[4-(trans-4-pentylcyclohexyl)-4'-biphenyl]-4-tert.butyl-2-oxaxoline;

(S)-2-[4-(trans-4-hepylcyclohexyl)-4'-biphenyl]-4-tert.butyl-2-oxaxoline;

(S)-2-(4-[1-(trans-4-pentylcyclohexyl(-2-ethyl]phenyl)-2-isopropyl-2-oxaxoline;

(S)-2-(4-[(trans-4-pentylcyclohexyl)methoxy]phenyl)-2-isopropyl-2-oxaxoline;
(S)-2-(4-[3-(trans-4-pentylcyclohexyl)-1-propyloxy]phenyl)-2-isopropyl-2-oxaxoline;
(S)-2-(4-[(E)-3-(trans-4-pentylcyclohexyl)allyloxy]phenyl)-2-isopropyl-2-oxaxoline, m.p. 62° C.;
(S)-2-(4-[4-(trans-4-pentylcyclohexyl)-1-butyl]phenyl)-2-isopropyl-2-oxaxoline;
(S)-2-(4-[4(E)-(trans-4-pentylcyclohexyl)-3-butenyl]phenyl)-2-isopropyl-2-oxaxoline;
2,2'-(2,6-naphthyl)-bis-(S)-isopropyl-2-oxaxoline, m.p. 182° C.;
2,2'-(2,6-naphthyl)-bis-(S)-tert.butyl-2-oxaxoline;
2,2'-(1,4-phenyl)-bis-(S)-isopropyl-2-oxaxoline;
2,2'-(1,4-phenyl)-bis-(S)-tert.butyl-2-oxaxoline;
2,2'-(4,4'-biphenyl)-bis-(S)-isopropyl-2-oxaxoline;
2,2'-(4,4'-biphenyl)-bis-(S)-tert.butyl-2-oxaxoline;
(S)-2-(4-fluorophenyl)-4-isopropyl-2-oxaxoline;
(S)-2-(4-chlorophenyl)-4-isopropyl-2-oxaxoline;
(S)-2-(4-bromophenyl)-4-isopropyl-2-oxaxoline;
(S)-2-(4-cyanophenyl)-4-isopropyl-2-oxaxoline;
(S)-2-(4-methylphenyl)-4-isopropyl-2-oxaxoline;
(S)-2-(4-ethylphenyl)-4-isopropyl-2-oxaxoline;
(S)-2-(4-propylphenyl)-4-isopropyl-2-oxaxoline, colourless liquid;
(S)-2-(4-butylphenyl)-4-isopropyl-2-oxaxoline;
(S)-2-(4-pentylphenyl)-4-isopropyl-2-oxaxoline;
(S)-2-(4-hexylphenyl)-4-isopropyl- 2-oxaxoline;
(S)-2-(4-heptylphenyl)-4-isopropyl-2-oxaxoline;
(S)-2-(4-octylphenyl)-4-isopropyl-2-oxaxoline;
(S)-2-(4-methoxyphenyl)-4-isopropyl-2-oxaxoline;
(S)-2-(4- ethoxyphenyl)-4-isopropyl-2-oxaxoline;
(S)-2-(4-propyloxyphenyl)-4-isopropyl-2-oxaxoline;
(S)-2-(4-butyloxyphenyl)-4-isopropyl-2-oxaxoline;
(S)-2-(4-pentyloxyphenyl)-4-isopropyl-2-oxaxoline;
(S)-2-(4-hexyloxyphenyl)-4-isopropyl-2-oxaxoline;
(S)-2-(4-heptyloxyphenyl)-4-isopropyl-2-oxaxoline, m.p. 31° C.;
(S)-2-(4-fluoro-4'-biphenyl)-4-isopropyl-2-oxaxoline;
(S)-2-(4-chloro-4'-biphenyl)-4-isopropyl-2-oxaxoline;
(S)-2-(4-bromo-4'-biphenyl)-4-isopropyl-2-oxaxoline;
(S)-2-(4-cyano-4'-biphenyl)-4-isopropyl-2-oxaxoline;
(S)-2-(4-methyl-4'-biphenyl)-4-isopropyl-2-oxaxoline;
(S)-2-(4-ethyl-4'-biphenyl)-4-isopropyl-2-oxaxoline;
(S)-2-(4-propyl-4'-biphenyl)-4-isopropyl-2-oxaxoline;
(S)-2-(4-butyl -4'-biphenyl)-4-isopropyl-2-oxaxoline;
(S)-2-(4-pentyl-4'-biphenyl)-4-isopropyl-2-oxaxoline;
(S)-2-(4-methoxy-4'-biphenyl)-4-isopropyl-2-oxaxoline;
(S)-2-(4-ethoxy-4'-biphenyl)-4-isopropyl-2-oxaxoline;
(S)-2-(4-propyloxy-4'-biphenyl)-4-isopropyl-2-oxaxoline;
(S)-2-(4-butyloxy-4'-biphenyl)-4-isopropyl-2-oxaxoline;
(S)-2-(4-pentyloxy-4'-biphenyl)-4-isopropyl-2-oxaxoline, m.p. 125° C.;
(S)-2-(4-heptyloxy-4'-biphenyl)- 4-isopropyl-2-oxaxoline;
(S)-2-[trans-4-(trans-4-pentylcyclohexyl)cyclohexyl]-4-isopropyl-2-oxazoline, m.p. (C-$S_B$) 38° C., cl.p. ($S_B$-N) 126° C.

EXAMPLE 2

(S)-2-(4-Carboxyphenyl)-4-isopropyl-2-oxazoline (2.0 g), 0.5 g of methyl (S)-lactate and 0.1 g of 4-(dimethylamino)pyridine are dissolved in 50 ml of dichloromethane and the solution is treated portionwise with 1.4 g of N,N'-dicyclohexylcarbodiimide within 10 minutes while stirring. The mixture is stirred at room temperature overnight and then filtered. The filtrate is diluted with dichloromethane, washed twice with 50 ml of saturated sodium carbonate solution each time and then with water, dried over magnesium sulphate and concentrated. The crude product obtained is purified by chromatography on silica gel with toluene. The (S)-2-[4-([(S)-1-(methoxycarbonyl)-1-ethoxy]carbonyl)phenyl]-4-isopropyl-2-oxazoline obtained is recrystallized from ethanol;

The (S)-2-(4-carboxyphenyl)-4-isopropyl-2-oxazoline used as the starting material is prepared as follows:

A mixture of 3 g of (S)-2-(4-[methoxycarbonyl]phenyl)-4-isopropyl-2-oxazoline, 3 g of potassium hydroxide, 5 ml of water and 50 ml of methanol is heated at 75° C. on an oil bath for 4 hours. The cooled mixture is treated with 10 ml of ice-cold 3N hydrochloric acid and the liberated acid is taken up in 150 ml of diethyl ether. The separated aqueous phase is back-extracted twice with 100 ml of diethyl ether each time. The combined organic phases are washed with 50 ml of 2N sodium carbonate solution and several times with water, dried over magnesium sulphate and concentrated. Recrystallization of the resulting crude product from ethanol yields (S)-2-(4-carboxyphenyl)-4-isopropyl-2-oxazoline.

The following compounds can be produced in an analogous manner:

(S)-2-[4-([(S)-1-(ethoxycarbonyl)-1-ethoxy]carbonyl)phenyl]-4-isopropyl-2-oxazoline;
(S)-2-[4-([(S)-1-(propyloxycarbonyl)-1-ethoxy]carbonyl)-phenyl]-4-isopropyl-2-oxazoline;
(S)-2-[4-([(S)-1-(butyloxycarbonyl)-1-ethoxy]carbonyl)-phenyl]-4-isopropyl-2-oxazoline;
(S)-2-[4-([(S)-2-octyl]carbonyl)phenyl]-4-isopropyl-2-oxazoline and the optical antipodes of the said compounds.

EXAMPLE 3

The following liquid crystal basic mixture BM-1 was used to measure the induced pitch and its temperature dependence in liquid crystal materials:

| | |
|---|---|
| 5.36 wt. % of | 4'-ethyl-4-cyanobiphenyl, |
| 3.18 wt. % of | 4'-propyl-4-cyanobiphenyl, |
| 6.08 wt. % of | 4'-butyl-4-cyanobiphenyl, |
| 6.53 wt. % of | 4-(trans-4-propylcyclohexyl)benzonitrile, |
| 14.67 wt. % of | 4-(trans-4-pentylcyclohexyl)benzonitrile, |
| 5.21 wt. % of | 4-ethyl-1-(trans-4-propylcyclohexyl)benzene, |
| 16.54 wt. % of | 4-ethoxy-1-[2-(trans-4-propylcyclohexyl)ethyl]benzene, |
| 5.0 wt. % of | 4''-pentyl-4-cyano-p-terphenyl, |
| 5.71 wt. % of | 4'-(trans-4-pentylcyclohexyl)-4-cyanobiphenyl, |
| 15.95 wt. % of | 1-[2-(trans-4-butylcyclohexyl)ethyl]-4-(trans-4-pentylcyclohexyl)benzene, |
| 4.74 wt. % of | 4-[2-(trans-4-butylcyclohexyl)ethyl]-4'-(trans-4-pentylcyclohexyl)biphenyl, |
| 7.59 wt. % of | 4-[2-(trans-4-butylcyclohexyl)ethyl]-4'-(trans-4-pentylcyclohexyl)-1,1'-ethylenedibenzene, |
| 2.84 wt. % of | trans-4-[2-(trans-4-propylcyclohexyl)ethyl]-cyclohexanecarboxylic acid 4-cyanophenyl ester; | m.p. < −30° C., cl.p. (N-I) 90° C.; $\Delta\epsilon = 8.5$, $\Delta n = 0.139$ and $\eta = 22$ mPa.s measured at 22° C.

Liquid crystal basic mixture BM-1 was treated with each of the following optically active dopants:

D-1 = (S)-2-[4-(trans-4-heptylcyclohexyl)phenyl]-4-isopropyl-2-oxazoline,

D-2=2,2'-(2,6-naphthyl)-bis-(S)-isopropyl-2-oxazoline.

The results compiled in Table 1 were obtained for the chiral doped mixtures, whereby A, B and C denote the parameters of the equation $$\backslash F(1,pc) = A + BT_1 CT \backslash S(2,1)$$

and p, c and $T_1$ have the following significances
$T_1 = T-22°$ C.
T = temperature in °C.
p = pitch in mm (a positive value signifies a clockwise helical structure and a negative value signifies an anticlockwise helical structure)
c = concentration of the optically active dopant in wt. %.

TABLE 1

| Mixture | Dopant | A  [$10^{-2} \cdot \mu m^{-1} \cdot wt. \%^{-1}$] | B  [$10^{-4} \cdot \mu m^{-1} \cdot wt. \%^{-1} \cdot °C.^{-1}$] | C  [$10^{-6} \cdot \mu m^{-1} \cdot wt. \%^{-1} \cdot °C.^{-2}$] | p · c (from 22° C.)  [$\mu m \cdot wt. \%$] |
|---|---|---|---|---|---|
| M-1 | 1.0 wt. % D-1 | −5.36 | 0.805 | 0.800 | −18.65 |
| M-2 | 1.0 wt. % D-2 | +5.75 | 1.234 | 0.656 | +17.39 |

A solution of 0.8 g of (S)-2-(4-formylphenyl)-4-isopropyl-2-oxazoline and 1 g of dimethyl L(+)-tartrate in 50 ml of toluene is treated with 0.1 g of toluene-4-sulphonic acid. The mixture is heated to boiling for 2.5 hours and the water formed is distilled off simultaneously. Then, 4 drops of triethylamine are added to the reaction mixture. After cooling the mixture is washed with 20 ml of 1N sodium hydrogen carbonate solution and twice with 20 ml of water each time, dried over sodium sulphate and concentrated. Chromatography of the residue on silica gel with toluene/ethyl acetate (vol. 1:1) and recrystallization from ethanol gives pure dimethyl (4R,5R)-2-(4-[(S)-4-isopropyl-2-oxazolinyl]-phenyl)-1,3-dioxolane-4,5-dicarboxylate The (S)-2-(4-formylphenyl)-4-isopropyl-2-oxazoline used as the starting material is prepared as follows:

A solution of 2 g of (S)-2-(4-bromophenyl)-4-isopropyl-2-oxazoline in 20 ml of absolute tetrahydrofuran is treated drop-wise with 5 ml of 1.6M butyllithium in hexane at −78° C. and while gassing with nitrogen, stirred at this temperature for 2 hours, then treated dropwise with 2 ml of absolute N,N-dimethyl-formamide and then warmed slowly to room temperature. The reaction mixture is poured into 100 ml of water and extracted three times with 50 ml of diethyl ether each time. The combined organic phases are washed twice with 100 ml of saturated sodium chloride solution each time, dried over magnesium sulphate, filtered and then concentrated. Chromatography of the residue on silica gel with hexane/ethyl acetate (vol. 9:1) yields 0.8 g of pure (S)-2-(4-formylphenyl)-4-isopropyl-2-oxazoline.

The following compounds can be produced in an analogous manner:

diethyl (4R,5R)-2-(4-[(S)-4-isopropyl-2-oxazolinyl]-phenyl)-1,3-dioxolane-4,5-dicarboxylate;
diisopropyl (4R,5R)-2-(4-[(S)-4-isopropyl-2-oxazolinyl]-phenyl)-1,3-dioxolane-4,5-dicarboxylate;
dibutyl (4R,5R)-2-(4-[(S)-4-isopropyl-2-oxazolinyl]-phenyl)-1,3-dioxolane-4,5-dicarboxylate;
dimethyl (4R,5R)-2-(4-[(S)-4-tert.butyl-2-oxazolinyl]-phenyl)-1,3-dioxolane-4,5-dicarboxylate;
diethyl (4R,5R)-2-(4-[(S)-4-tert.butyl-2-oxazolinyl]-phenyl)-1,3-dioxolane-4,5-dicarboxylate;
diisopropyl (4R,5R)-2-(4-[(S)-4-tert.butyl-2-oxazolinyl]-phenyl)-1,3-dioxolane-4,5-dicarboxylate
dibutyl (4R,5R)-2-(4-[(S)-4-tert.butyl-2-oxazolinyl]-phenyl)-1,3-dioxolane-4,5-dicarboxylate.

EXAMPLE 5

(R)-2-(4-Formylphenyl)-4-isopropyl-2-oxazoline (1.0 g), 1.0 g of (2S,3R)-2-octyl-1,3-butanediol and 0.1 g of p-toluenesulphonic acid in 50 ml of absolute toluene are reacted in an analogous manner to Example 4 to give 2-(4-[2S,4R,5S]-4-methyl-5-octyl-m-dioxan-2-yl]phenyl)-(R)-4-isopropyl-2-oxazoline.

The following compounds can be produced in an analogous manner:

2-(4-[2S,4R,5S]-4-methyl-5-methyl-m-dioxan-2-yl]phenyl)-(R)-4-isopropyl-2-oxaxoline;
2-(4-[2S,4R,5S]-4-methyl-5-ethyl-m-dioxan-2-yl]phenyl)-(R)-4-isopropyl-2-oxaxoline;
2-(4-[2S,4R,5S]-4-methyl-5-propyl-m-dioxan-2-yl]phenyl)-(R)-4-isopropyl-2-oxaxoline;
2-(4-[2S,4R,5S]-4-methyl-5-butyl-m-dioxan-2-yl]phenyl)-(R)-4-isopropyl-2-oxaxoline;
2-(4-[2S,4R,5S]-4-methyl-5-pentyl-m-dioxan-2-yl]phenyl)-(R)-4-isopropyl-2-oxaxoline;
2-(4-[2S,4R,5S]-4-methyl-5-hexyl-m-dioxan-2-yl]phenyl)-(R)-4-isopropyl-2-oxaxoline;
2-(4-[2S,4R,5S]-4-methyl-5-heptyl-m-dioxan-2-yl]phenyl)-(R)-4-isopropyl-2-oxaxoline;
2-(4-[2S,4R,5S]-4-methyl-5-vinyl-m-dioxan-2-yl]phenyl)-(R)-4-isopropyl-2-oxaxoline;
2-(4-[2S,4R,5S]-4-methyl-5-allyl-m-dioxan-2-yl]phenyl)-(R)-4-isopropyl-2-oxaxoline;
2-(4-[2S,4R,5S]-4-methyl-5-(3-butenyl)-m-dioxan-2-yl]phenyl)-(R)-4-isopropyl-2-oxaxoline;
2-(4-[2S,4R,5S]-4-methyl-5-(4-pentenyl)-m-dioxan-2-yl]phenyl)-(R)-4-isopropyl-2-oxaxoline;
2-(4-[2S,4R,5S]-4-methyl-5-methyl-m-dioxan-2-yl]phenyl)-(R)-4-tert.butyl-2-oxaxoline;
2-(4-[2S,4R,5S]-4-methyl-5-ethyl-m-dioxan-2-yl]phenyl)-(R)-4-tert.butyl-2-oxaxoline;
2-(4-[2S,4R,5S]-4-methyl-5-propyl-m-dioxan-2-yl]phenyl)-(R)-4-tert.butyl-2-oxaxoline;
2-(4-[2S,4R,5S]-4-methyl-5-butyl-m-dioxan-2-yl]phenyl)-(R)-4-tert.butyl-2-oxaxoline;
2-(4-[2S,4R,5S]-4-methyl-5-pentyl-m-dioxan-2-yl]phenyl)-(R)-4-tert.butyl-2-oxaxoline;
2-(4-[2S,4R,5S]-4-methyl-5-hexyl-m-dioxan-2-yl]phenyl)-(R)-4-tert.butyl-2-oxaxoline;
2-(4-[2S,4R,5S]-4-methyl-5-heptyl-m-dioxan-2-yl]phenyl)-(R)-4-tret.butyl-2-oxaxoline;
2-(4-[2S,4R,5S]-4-methyl-5-octyl-m-dioxan-2-yl]phenyl)-(R)-4-tert.butyl-2-oxaxoline;
2-(4-[2S,4R,5S]-4-methyl-5-vinyl-m-dioxan-2-yl]phenyl)-(R)-4-tert.butyl-2-oxaxoline;
2-(4-[2S,4R,5S]-4-methyl-5-allyl-m-dioxan-2-yl]phenyl)-(R)-4-tert.butyl-2-oxaxoline;

2-(4-[2S,4R,5S]-4-methyl-5-(3-butenyl)-m-dioxan-2-yl]phenyl)-(R)-4-tert.butyl-2-oxaxoline;
2-(4-[2S,4R,5S]-4-methyl-5-(4-pentenyl)-m-dioxan-2-yl]phenyl)-(R)-4-tert.butyl-2-oxaxoline.

What is claimed is:

1. An optically active compound of the formula

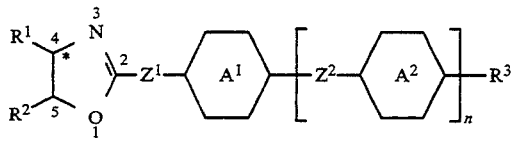

wherein n is the number 0 or 1; $R^3$ is a group $R^4$ or a group of the formula

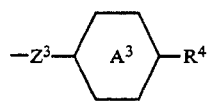

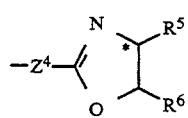

$A^1$ and $A^2$ each independently represent 1,4-phenylene, which is unsubstituted or mono- or multiply-substituted with halogen trans-1,4-cyclohexylene; trans-1,3-dioxane-2,5-diyl or naphthalene-2,6-diyl with the proviso that not both rings A1 and A2 are 1,4-phenylene when R3 is a group R4; A3 is trans-1,4-cyclohexylene; $Z^1$ and $Z^4$ each independently represent a single covalent bond or —CH$_2$CH$_2$—; $Z^2$ and $Z^3$ each independently denote a single covalent bond, —CH$_2$CH$_2$—, or the trans form of —CH=CH—CH$_2$CH$_2$—, —CH$_2$CH$_2$—CH=CH—, —CH=CH—CH$_2$O— or —OCH$_2$—CH=CH—; $R^1$ and $R^5$ each independently is alkyl with 1 to 12 carbon atoms, alkoxymethyl with 2 to 12 carbon atoms, p-alkoxyphenyl or p-alkoxybenzyl; $R^2$ and $R^6$ each independently is hydrogen, alkyl with 1 to 12 carbon atoms or phenyl; $R^4$ denotes hydrogen, halogen, cyano, trifluoromethyl, trifluoromethoxy or alkyl with 1 to 12 carbon atoms or alkenyl with 2 to 12 carbon atoms respectfully, in which alkyl, alkenyl or one methylene group can be replaced by —O—, —COO— and/or —OOC—; and the oxazoline ring in formula I is present in optically active form, with the proviso that at least one of the groups $Z^1$ and $Z^4$ is —CH$_2$CH$_2$— when ring $A^1$ is 1,4-phenylene, n is O and $R^3$ is a group of formula III.

2. The optically active compound according to claim 1 and having the formula

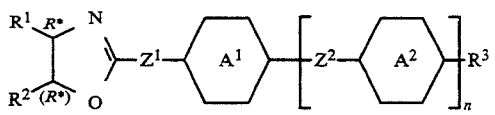

wherein n is the number 0 or 1; $R^3$ is a group $R^4$ or a group of the formula

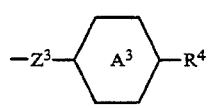

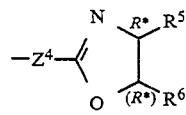

wherein the chiral center (R*) is absent when $R^2$ is hydrogen, and stands for R* when $R^2$ is different from hydrogen; and the asymmetric carbon atoms denoted by R* are all present in the R-configuration or are all present in the S-configuration.

3. The optically active compound according to claim 1, wherein one of groups $Z^2$ and $Z^3$ denotes a single covalent bond or —CH$_2$CH$_2$— and the other of groups $Z^2$ and $Z^3$ denotes a single covalent bond.

4. The optically active compound according to claim 1, wherein $R^4$ denotes halogen, cyano, trifluoromethyl, trifluoromethoxy, unsubstituted alkyl, alkenyl, alkoxy, alkenyloxy, 1-(alkoxycarbonyl)-ethoxy or 1-(alkoxycarbonyl)ethoxycarbonyl having 1to 7 carbon atoms.

5. A liquid crystalline mixture containing a liquid crystalline carrier material and one or more optically active compounds of the formula

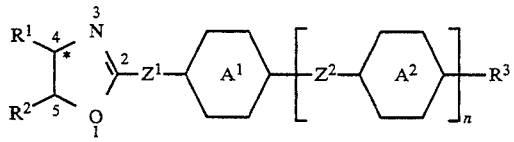

wherein n is the number 0 or 1; $R^3$ is a group $R^4$ or a group of the formula

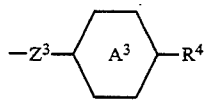

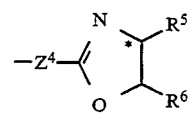

$A^1$ and $A^2$ each independently represent 1,4-phenylene; trans-1,4-cyclohexylene; trans-1,3-dioxane-2,5-diyl or naphthalene-2,6-diyl with the proviso that not both rings $A^1$ and $A^2$ are 1,4-phenylene when $R^3$ is a group $R^4$; $A^3$ is trans-1,4-cyclohexylene; $Z^1$ and $Z^4$ each independently represent a single covalent bond or —CH$_2$CH$_2$—; $Z^2$ and $Z^3$ each independently denote a single covalent bond, —CH$_2$CH$_2$—, or the trans form of —CH=CH—CH$_2$CH$_2$ —, —CH$_2$CH$_2$—CH=CH—, —CH=CH—CH$_2$O— or —OCH$_2$—CH=CH—; $R^1$ and $R^5$ each independently is alkyl with 1 to 12 carbon atoms, alkoxymethyl with 2 to 12 carbon atoms, p-alkoxyphenyl or p-alkoxybenzyl; $R^2$ and $R^6$ each independently is hydrogen, alkyl with 1 to 12 carbon atoms or phenyl; $R^4$ denotes hydrogen, halogen, cyano, trifluoromethyl, trifluoromethoxy or alkyl with 1 to 12 carbon atoms or alkenyl with 2 to 12 carbon atoms respectively, in which alkyl, alkenyl or one methylene group can be replaced by —O—, —COO— and/or —OOC—; and the oxazoline ring in formula I is present in optically active form, with the proviso that at least one of the groups $Z^1$ and $Z^4$ is —CH$_2$CH$_2$— when ring $A^1$ is 1,4-phenylene, n is O and $R^3$ is a group of formula III.

* * * * *